US008753611B2

(12) United States Patent
Eichman et al.

(10) Patent No.: US 8,753,611 B2
(45) Date of Patent: *Jun. 17, 2014

(54) SUBLINGUAL BUCCAL EFFERVESCENT

(75) Inventors: Jonathan D. Eichman, Ann Arbor, MI (US); John Hontz, Plymouth, MN (US); Rajendra K. Khankari, Maple Grove, MN (US); Sathasivan Indiran Pather, Plymouth, MN (US); Joseph R. Robinson, Madison, WI (US)

(73) Assignee: Cephalon, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,003

(22) Filed: May 2, 2011

(65) Prior Publication Data

US 2011/0223115 A1   Sep. 15, 2011

Related U.S. Application Data

(63) Continuation of application No. 12/429,475, filed on Apr. 24, 2009, which is a continuation of application No. 09/661,693, filed on Sep. 14, 2000, now abandoned, which is a continuation of application No. 09/327,814, filed on Jun. 8, 1999, now Pat. No. 6,200,604, which is a continuation of application No. 09/277,424, filed on Mar. 26, 1999, now abandoned.

(60) Provisional application No. 60/079,652, filed on Mar. 27, 1998.

(51) Int. Cl.
*A01N 25/02* (2006.01)
*A61K 9/12* (2006.01)
*A61F 13/00* (2006.01)
*A61K 9/20* (2006.01)
*A61K 9/46* (2006.01)

(52) U.S. Cl.
USPC ............ 424/43; 424/44; 424/434; 424/466; 424/464

(58) Field of Classification Search
USPC .............................. 424/43, 44, 434, 466, 464
See application file for complete search history.

(56) References Cited

U.S. PATENT DOCUMENTS

| | | |
|---|---|---|
| 1,262,888 A | 4/1918 | Westlake |
| 2,887,437 A | 5/1959 | Klioze et al. |
| 3,042,531 A | 7/1962 | Leal et al. |
| 3,131,123 A | 4/1964 | Masquelier |
| 3,577,490 A | 5/1971 | Welsh et al. |
| 3,888,976 A | 6/1975 | Mlkvy et al. |
| 3,961,041 A | 6/1976 | Nishimura et al. |
| 3,962,417 A | 6/1976 | Howell |
| 3,972,995 A | 8/1976 | Tsuk et al. |
| 4,147,768 A | 4/1979 | Shaffer et al. |
| 4,187,286 A | 2/1980 | Marcus |
| 4,289,751 A | 9/1981 | Windhueser |
| 4,370,160 A | 1/1983 | Ziemelis |
| 4,443,428 A | 4/1984 | Oshlack et al. |
| 4,493,848 A | 1/1985 | LaHann et al. |
| 4,503,031 A | 3/1985 | Glassman |
| 4,599,342 A | 7/1986 | LaHann |
| 4,613,497 A | 9/1986 | Chavkin |
| 4,639,368 A | 1/1987 | Niazi et al. |
| 4,671,953 A | 6/1987 | Stanley et al. |
| 4,687,662 A | 8/1987 | Schobel |
| 4,689,218 A | 8/1987 | Gazzaniga et al. |
| 4,717,723 A | 1/1988 | Sugden |
| 4,725,427 A | 2/1988 | Ashmead et al. |
| 4,753,792 A | 6/1988 | Aberg |
| 4,756,710 A | 7/1988 | Bondi et al. |
| 4,853,211 A | 8/1989 | Kurobe et al. |
| 4,863,737 A | 9/1989 | Stanley et al. |
| 4,876,039 A | 10/1989 | Lo et al. |
| 4,940,588 A | 7/1990 | Sparks et al. |
| 5,002,771 A | 3/1991 | Purkaystha et al. |
| 5,004,601 A | 4/1991 | Snipes |
| 5,028,411 A | 7/1991 | Callingham et al. |
| 5,053,396 A | 10/1991 | Blass |
| 5,055,306 A | 10/1991 | Barry et al. |
| 5,073,374 A | 12/1991 | McCarty |
| 5,102,665 A | 4/1992 | Schaeffer |
| 5,102,666 A | 4/1992 | Acharya |
| 5,135,752 A | 8/1992 | Snipes |
| 5,178,878 A | 1/1993 | Wehling et al. |
| 5,223,264 A * | 6/1993 | Wehling et al. ............... 424/466 |

(Continued)

FOREIGN PATENT DOCUMENTS

| | | |
|---|---|---|
| CA | 2211586 | 8/1996 |
| CA | 2218370 | 2/1997 |

(Continued)

OTHER PUBLICATIONS

Order—In the United States District Court for the district of Delaware, Cephalon, Inc., and CIMA Labs, Inc., Civil No. 08-330-SLR, Mar. 11, 2011.

Plaintiffs' Amended Notice of Appeal to the United States Court of Appeals for the Federal Circuit, Case: 1:08-cv-00330-SLR, Document 339 Filed Apr. 26, 2011.

Notice of Docketing, United States Court of Appeals for the Federal Circuit, Case: 1:08-cv-00330-SLR, Document 340, Filed May 9, 2011.

Brief for Plaintiffs-Appellants, United States Court of Appeals for the Federal Circuit, *Cephalon, Inc.* and *CIMA Labs, Inc.*, Appeal No. 2011-1325, dated Nov. 16, 2011.

(Continued)

*Primary Examiner* — Sreeni Padmanabhan
*Assistant Examiner* — Uma Ramachandran

(57) ABSTRACT

A pharmaceutical dosage form adapted to supply a medicament to the oral cavity for buccal, sublingual or gingival absorption of the medicament which contains an orally administrable medicament in combination with an effervescent for use in promoting absorption of the medicament in the oral cavity. The use of an additional pH adjusting substance in combination with the effervescent for promoting the absorption drugs is also disclosed.

11 Claims, No Drawings

(56) References Cited

U.S. PATENT DOCUMENTS

| | | |
|---|---|---|
| 5,234,957 A | 8/1993 | Mantelle |
| 5,288,497 A | 2/1994 | Stanley et al. |
| 5,314,904 A | 5/1994 | Egidio et al. |
| 5,387,420 A | 2/1995 | Mitchell et al. |
| 5,401,513 A | 3/1995 | Wehling et al. |
| 5,445,827 A | 8/1995 | Fritsch et al. |
| 5,458,879 A | 10/1995 | Singh et al. |
| 5,464,632 A | 11/1995 | Cousin et al. |
| 5,468,504 A | 11/1995 | Schaeffer |
| 5,501,861 A | 3/1996 | Makino |
| 5,503,846 A | 4/1996 | Wehling et al. |
| 5,550,861 A | 8/1996 | Chan et al. |
| 5,559,096 A | 9/1996 | Edwards et al. |
| 5,607,697 A | 3/1997 | Alkire et al. |
| 5,624,687 A | 4/1997 | Yano et al. |
| 5,626,866 A | 5/1997 | Ebert et al. |
| 5,635,210 A | 6/1997 | Allen, Jr. et al. |
| 5,646,151 A | 7/1997 | Kruse et al. |
| 5,656,284 A | 8/1997 | Balkin |
| 5,720,974 A | 2/1998 | Makino et al. |
| 5,785,989 A | 7/1998 | Stanley et al. |
| 5,807,688 A | 9/1998 | Blackburn et al. |
| 5,851,553 A | 12/1998 | Myers et al. |
| 5,853,748 A | 12/1998 | New |
| 5,900,252 A | 5/1999 | Calanchi et al. |
| 5,948,389 A | 9/1999 | Stein |
| 5,952,004 A | 9/1999 | Rudnic et al. |
| 5,958,455 A | 9/1999 | Roser et al. |
| 5,958,458 A | 9/1999 | Norling et al. |
| 6,034,085 A | 3/2000 | Joshi et al. |
| 6,068,853 A | 5/2000 | Giannos et al. |
| 6,071,539 A * | 6/2000 | Robinson et al. ............. 424/466 |
| 6,106,861 A | 8/2000 | Chauveau et al. |
| 6,117,912 A | 9/2000 | Disanto |
| 6,129,906 A | 10/2000 | Steventon |
| 6,155,423 A | 12/2000 | Katzner et al. |
| 6,171,617 B1 | 1/2001 | Gruber |
| 6,190,697 B1 | 2/2001 | Gergely et al. |
| 6,200,604 B1 | 3/2001 | Pather et al. |
| 6,242,002 B1 | 6/2001 | Tritthart et al. |
| 6,262,062 B1 | 7/2001 | Clemens |
| 6,264,981 B1 | 7/2001 | Zhang et al. |
| 6,284,274 B1 | 9/2001 | Merrill et al. |
| 6,316,027 B1 | 11/2001 | Clarke et al. |
| 6,326,360 B1 | 12/2001 | Kanazawa et al. |
| 6,326,384 B1 | 12/2001 | Whittle et al. |
| 6,350,470 B1 | 2/2002 | Pather et al. |
| 6,368,625 B1 | 4/2002 | Siebert et al. |
| 6,391,335 B1 | 5/2002 | Pather et al. |
| 6,488,961 B1 | 12/2002 | Robinson et al. |
| 6,509,036 B2 | 1/2003 | Pather et al. |
| 6,576,250 B1 | 6/2003 | Pather et al. |
| 6,641,838 B2 | 11/2003 | Pather et al. |
| 6,680,071 B1 | 1/2004 | Johnson et al. |
| 6,759,059 B1 | 7/2004 | Petterson et al. |
| 6,761,910 B1 | 7/2004 | Petterson et al. |
| 6,764,696 B2 | 7/2004 | Pather et al. |
| 6,835,194 B2 | 12/2004 | Johnson et al. |
| 7,670,617 B2 | 3/2010 | Pather et al. |
| 2001/0006677 A1 | 7/2001 | McGinity et al. |
| 2001/0041165 A1 | 11/2001 | Katdare et al. |
| 2002/0160991 A1 | 10/2002 | Shao |
| 2003/0035839 A1 | 2/2003 | Hirsh |
| 2004/0213855 A1 | 10/2004 | Petterson et al. |
| 2005/0037072 A1 | 2/2005 | Pather et al. |
| 2005/0042281 A1 | 2/2005 | Singh et al. |
| 2006/0292219 A1 | 12/2006 | Pather et al. |
| 2007/0036853 A1 | 2/2007 | Agarwal et al. |
| 2008/0131508 A1 | 6/2008 | Agarwal et al. |
| 2009/0214442 A1 | 8/2009 | Agarwal et al. |

FOREIGN PATENT DOCUMENTS

| | | |
|---|---|---|
| CA | 2254060 | 11/1997 |
| CA | 2326502 | 7/1999 |
| DE | 4139883 | 6/1993 |
| EP | 0197504 | 10/1986 |
| EP | 0275834 | 7/1988 |
| EP | 0354973 | 2/1990 |
| EP | 0361680 | 4/1990 |
| EP | 0396335 | 11/1990 |
| EP | 0737473 | 10/1996 |
| EP | 0839526 | 5/1998 |
| EP | 1062952 | 12/2000 |
| EP | 1067905 | 1/2001 |
| FR | 2732217 | 10/1996 |
| GB | 3160 | 0/1872 |
| GB | 1212704 | 11/1970 |
| GB | 2307857 | 6/1997 |
| JP | 7277959 | 10/1995 |
| NL | 7302521 | 8/1974 |
| TW | 36236 | 4/1981 |
| TW | 40484 | 12/1981 |
| WO | WO9104757 | 4/1991 |
| WO | WO 9104757 * | 4/1991 |
| WO | WO9302662 | 2/1993 |
| WO | WO9507701 | 3/1995 |
| WO | WO9527482 | 10/1995 |
| WO | WO9534291 | 12/1995 |
| WO | WO9629993 | 10/1996 |
| WO | WO9706786 | 2/1997 |
| WO | WO9717067 | 5/1997 |
| WO | WO9718796 | 5/1997 |
| WO | WO9945934 | 9/1999 |
| WO | WO9949842 | 10/1999 |
| WO | WO0059423 | 1/2000 |
| WO | WO0009093 | 2/2000 |
| WO | WO0035418 | 6/2000 |
| WO | WO0057858 | 10/2000 |
| WO | WO0180822 | 11/2001 |
| WO | WO2004067004 | 12/2004 |
| WO | WO2005065317 | 7/2005 |
| WO | WO2005065318 | 7/2005 |
| WO | WO2005065319 | 7/2005 |

OTHER PUBLICATIONS

Brief for defendants Appellees, United States Court of Appeals for the Federal Circuit, *Cephalon, Inc.* and *CIMA Labs, Inc.*, Appeal No. 2011-1325, dated May 18, 2012.

Alternative Routes of Drug Administration—Advantages and Disadvantages (Subject Review), American Academy of Pediatrics Committee on Drugs, Pediatrics, vol. 100(1), pp. 143, 147, Jul. 1997.

Altomare, E. et al., "Bioavailability of a New Effervescent Tablet of Ibuprofen in Healthy Volunteers", Eur. J. Clin. Pharmacol. vol. 52, pp. 505-506, (1997).

Amighi, K. et al., "Peroral Sustained-Release Film-Coated Pellets as a Means to Overcome Physiochemical and Biological Drug-Related Problems", In Vitro Development and Evaluation, Drug Development and Industrial pharmacy, vol. 24(6), pp. 509-551 (1998).

Audus, K.L., "Buccal Epithelial Cell Cultures as a Model to Study Oral Mucosal Drug Transport and Metabolism", Oral Mucosal Drug Delivery, Chptr 6, pp. 101-115 (1996).

Audus, K.L. et al., "The Use of Cultured Epithelial and Endothelial Cells for Drug Transport and Metabolism Studies", Pharmaceutical Research, vol. 7(5), p. 435, (1990).

Aungst, B.J., "Oral Mucosal Permeation Enhancement: Possibilities and Limitations", Oral Mucosal Drug Deliver, Chptr 4, pp. 65-81 (1996).

Berko, S. et al., "Influence of pH Change on Drug Release from Rectal Suppositories", Die Pharmazie, vol. 55, p. 324, (Apr. 2000), Govi-Verlag Pharmazeutischer Verlag ChmH, Eshborn.

Bredenberg, Susanne, "New Concepts in Administration of Drugs in Tablet Form", Thesis (Comprehensive Summaries of Uppsala Dissertations from the Faculty of Pharmacy 287) pp. 1-77, (2003).

Chen et al., "Studies on Formulations of Fentanyl Buccal Adhesive Tablets", Zhongguo Yiyao Gongye Zazhi, vol. 28(3), pp. 129-131 (1997).

(56) References Cited

OTHER PUBLICATIONS

Clinical Pharmacology FDA Submission, Clinical Pharmacology and Biopharmaceutics Reviews, NDA 21-947, Fentanyl Effervescent Buccal Tablet DFS, pp. 1-86, 31 pages withheld, 2006.

Coluzzi et al., "Breakthrough Cancer Pain" A Randomized Trial Comparing Oral Transmucosal Fentanyl Citrate (OTFC®) and Morphine Sulfate Immediate Release (MSIR®), Pain vol. 91, pp. 123-130, (2001).

Conine, James W., "Special Tablets in Pharmaceutical Dosage Forms", Tablets, vol. 1, p. 329 (Herbert A. Lieberman et al. eds.) 1989.

Coster ltr to the Speaker, Leader and Director re: Protecting Funding for FDA Office of Generic Drugs in Final 2011 Budget, dated Mar. 18 2011.

Darwish, M. et al., "Absolute and Relative Bioavailability of Fentanyl Buccal Tablet and Oral Transmucosal Fentanyl Citrate", J. Clin. Pharmacol. vol. 47, pp. 343-350 (2007).

Darwish, M. et al., "Relative Bioavailability and Dose Proportionality of a Novel Effervescent Form of Fentanyl in Healthy Volunteers", Anesthesiology, vol. 103 A790, (Oct. 24, 2005).

Darwish, M. et al., "Pharmacokinetics and Dose Proportionality of Fentanyl Effervescent Buccal Tablets in Healthy Volunteers", Clin. Pharmacol. vol. 44(12), pp. 1279-1286, (2005).

DeGrande et al., "Specialized Oral Mucosal Drug Delivery Systems: Patches", Oral Mucosal Drug Delivery, Chptr 12, pp. 285-313 (1998).

Eichman, Jonathan D., "Increased Drug Absorption Through Carbonation: Assessment of Biological Membranes", A thesis submitted in partial fulfillment of the requirements for the degree of Master of Science (Pharmaceutics) at the University of WI-Madison, (1995).

Eichman, Jonathan D., "Mechanistic Studies in Effervescent-Induced Permeability Enhancement", Dissertation, U of WI-Madison, 1997, pp. 1-24, catalogued Sep. 18, 1998.

Eichman et al., "Mechanistic Studies on Effervescent-Induced Permeability Enhancement", Pharm. Res. vol. 15(6), pp. 925-930 (1998).

Eichman, Jonathan D., "The Influence of In-Vivo Carbonation on GI Physiological Processes and Drug Permeability", Eur. J. Pharmaceutics and Biopharmaceutics, vol. 44, pp. 33-38, (1997), catalogued Sep. 18, 1998.

EP Communication from EP Patent Office, EP Patent Application No. 04815715.0, dated Mar. 28, 2008.

EP Search Report for EP Patent Application No. EP 00919523 dated Apr. 29, 2002.

EP Supplemental Search Report for EP Patent Application No. 04815715 dated Nov. 14, 2007.

EP Search Report for EP Patent Application No. EP 00926341 dated Nov. 23, 2005.

Exhibits A-J, Redacted in its Entirety, Exhibit I, Memorandum Order dated Sep. 21, 2010, Exhibit J., Oct. 23, 2009, Memorandum, Order in re: Brimonidine Patent Litigation, Exhibit K, Feb. 9, 2011, Fish & Richardson ltr re: Ceph et al. v. Sandoz, Order Compelling Sandoz to Produce Documents.

Fentora® (Fentanyl Buccal Tablet) Label, 9 pages, Oct. 2007.

Fish & Richardson Ltr to Stronski, Ceph et al. v. Watson re: Alleged Deficiencies in Cephalon's Response to Watson's Interrogatory No. 2, dated May 29, 2009.

Giannos et al., "Temporally Controlled Drug Systems: Coupling of pH Oscillators with Membrane Diffusion", Journal of Pharmaceutical Sciences, vol. 84(5), pp. 539-543, May 1995.

Hagerstrom, Helene, "Polymer Gels as Pharmaceutical Dosage Forms", Thesis (Comprehensive Summaries of Uppsala Dissertations from the Faculty of Pharmacy 293) 2003.

Hagerstrom, Helene, "Polymer Gels as Pharmaceutical Dosage Forms: Rheological Performance and Physicochemical Interactions at the Gel-Mucus Interface for Formulations Intended for Mucosal Drug Delivery", Theses from Uppsala University: 3538—Polymer Gels as Pharmaceutical Dosage Forms, pp. 1-3, htto://ou blications. uu. se/theses/abstract.xsql?dbid=3538&lang=en, 2004.

Harris, D. et al., "Drug Delivery via the Mucous Membranes of the Oral Cavity", Journal of Pharmaceutical Sciences, vol. 81(1), pp. 1-10 (1992).

Hessell, P.G., et al., "A Comparison of the Availability of Prochlorperazine Following I.M. Buccal and Oral Administration", International Journal of Pharmaceutics, vol. 52(2), pp. 159-164, Jun. 1, 1989.

http://Chemical1and21.com/industrialchem/inorganic/Sodium%20Sulphate.htm, Sodium Sulfate, 2 pages, 2012.

Impax Lab, Paragraph IV Certification Notice, dated Oct. 6, 2011.

International Search Report for PCT Application No. PCT/US00/07567, dated Jul. 5, 2000.

International Search Report for PCT Application No. PCT/US04/43703, dated Nov. 1, 2005.

Kellaway et al., "Mucoadhesive Hydrogels for Buccal Delivery", Oral Mucosal Drug Delivery, Chptr. 10, pp. 221-237, (1996).

Kramer et al., "Pharmacodynamic Model of the Effects of Morphine and Morphine-6-Glucoronide During Patient-Controlled Analgesia", American Society for Clinical Pharmacology and Therapeutics, Clinical Pharmacology & Therapeutics, vol. 59(2), p. 132, Feb. 1996.

Labroo, RB et al., "Fentanyl Metabolism by Human Hepatic and Intestinal Cytochrome P450 3A4: Implications for Interindividual Variability in Disposition, Efficacy, and Drug Interactions", Drug Metabolism and Disposition, vol. 25(9): pp. 1072-1080, (1997).

Malpani, "Sodium Starch Glycolate", 13 pages, Jan. 5, 2010.

Mendes et al., "Chewable Tablets", Pharmaceutical Dosage Forms Tablets, Edited by H.A. Lieberman, $2^{nd}$ Edition, vol. 1, pp. 372-376, 1989.

Mylan et al. Notice of Paragraph IV Certification: Amendment to ANDA No. 202577 Fentanyl Citrate Buccal Tablets, (Flynn), dated Sep. 28, 2011.

Nishimura et al., "Dosage Form Design for Improvement of Bioavailability of Levodopa VI: Formulation of Effervescent Enteric-Coated Tablets", Journal of Pharmaceutical Sciences, vol. 73(7), Jul. 1984.

Notice of Reference re: U.S. Appl. No. 12/955,346, 2011.

Palmisano, Clinical Review of Fentanyl Oralet (Oral Transmucosal Fentanyl Citrate), NDA Application No. 20-195/S-002, dated Feb. 26, 1996.

U.S. Appl. No. 09/661,693, filed Sep. 14, 2000.

Pather et al., "Enhanced Buccal Delivery of Fentanyl Using the OraVescent Drug Delivery System", Buccal Delivery, vol. 1(1), 6 pages, Oct. 2001.

Physician's Desk Reference Actiq, pp. 1151-1155, 2004.

Physician's Desk Reference Kadian, pp. 569-573, 2005.

Portenoy et al., "Breakthrough Pain: Definition, Prevalence and Characteristics", Pain, vol. (41), pp. 273-281 (1990).

Portenoy et al., "Fentanyl Buccal Tablet (FBT) for Relief of Breakthrough Pain in Opioid-Treated Patients with Chronic Low Back Pain: A Randomized, Placebo-Controlled Study", Fentanyl Buccal Tablet for Breakthrough Pain, vol. 23(1), pp. 223-233, (2007).

Ranade, "Drug Delivery Systems 5B. Oral Drug Delivery", Drug Delivery Systems Series, J. Clin. Pharmaco., vol. 31, pp. 98-115, (1991).

Rassing, R. "Specialized Oral Mucosal Drug Delivery Systems: Chewing Gum", Oral Mucosal Drug Delivery, Chptr. 13, pp. 319-353, (1996).

Rathbone et al., "In Vivo Techniques for Studying the Oral Mucosal Absorption Characteristics of Drugs in Animals and Humans", Oral Mucosal Drug Delivery, Chptr. 7, pp. 121-151, (1996).

Rathbone et al., "Systemic Oral Mucosal Drug Delivery and Delivery Systems", Oral Mucosal Drug Delivery, Chptr 11, pp. 241-275 (1996).

Reisine et al., "Opioid Analgesics and Antagonists", in Hardman, J.G. et al., editors. Goodman and Gilman's Pharmacologic Basis of Therapeutics, $9^{th}$ Rev. Ed. New York: McGraw Hill, pp. 521-555, (1996).

Rowe et al., "Handbook of Pharmaceutical Excipients", Fifth Edition, pp. 758-759, (2006).

Sasahara et al., "Dosage Form Design for Improvement of Bioavailability of Levodopa II: Bioavailability of Marketed Levodopa Preparations in Dogs and Parkinsonian Patients", J. Pharm. Sci. vol. 69(3), pp. 261-265, (1980).

(56) References Cited

OTHER PUBLICATIONS

Sasahara et al., "Dosage Form Design for Improvement of Bioavailability of Levodopa III: Influence of Dose on Pharmacokinetic Behavior of Levodopa in Dogs and Parkinsonian Patients", J. Pharm. Sci. vol. 69(12), pp. 1374-1378, (1980).
Sasahara et al., "Dosage Form Design for Improvement of Bioavailability of Levodopa IV: Possible Causes of Low Bioavailability of Oral Levodopa in Dogs", J. Pharm. Sci., vol. 70(7), pp. 730-733, (1981).
Sasahara et al., "Dosage Form Design for Improvement of Bioavailability of Levodopa V: Absorption and Metabolism of Levodopa in Intestinal Segments of Dogs", J. Pharm. Sci., vol. 70(10), pp. 1157-1160, (1981).
Schenkels et al., "Salivary Mucins: Their Role in Oral Mucosal Barrier Function and Drug Delivery", Oral Mucosal Drug Delivery, Chptr 9, pp. 191-211, (1996).
Scott et al., "EEG Quantification of Narcotic Effect: The Comparative Pharmacodynamics of Fentanyl and Alfentanil", Anesthesiology, vol. 62: pp. 234-241 (1985).
Sorasuchart et al., "Drug Release from Spray Layered and Coated Drug-Containing Beads: Effects of pH and Comparison of Different Dissolution Methods", Drug Development and Industrial Pharmacy, vol. 25(10), pp. 1093-1098, (1999).
Soskolone et al., "Intra-periodontal Pocket Drug Delivery Systems", Oral Mucosal Drug Delivery, Chptr. 14, pp. 359-373, (1996).
Squier et al., "Structure and Function of the Oral Mucosa and Implications for Drug Delivery", Oral Mucosal Drug Delivery, Chptr. 1, pp. 1-19, (1996).
Stanley et al., "Novel Delivery Systems: Oral Transmucosal and Intranasal Transmucosal", Journal of Pain and Symptom Management, vol. 7(3): 163-171 (1992).
Sterne Kessler et al., Ltr re: Barr Supplemental Notification Pursuant to §505(j)(2)(B)(ii) of the Federal Food, Drug, and Cosmetic Act, 7 pages, Dated Dec. 22, 2008.
Sterne Kessler et al., Ltr. re: Supplemental Notification Pursuant to §505(j)(2)(B)(ii) of the Federal Food, Drug, and Cosmetic Act, 7 pages, Dated Jun. 27, 2008.
Sterne Kessler et al., Ltr. re: Notification Pursuant to §505(j)(2)(B)(ii) of the Federal Food, Drug, and Cosmetic Act, 9 pages, Dated Jun. 9, 2008.
Streisand et al., "Absorption and Bioavailability of Oral Transmucosal Fentanyl Citrate", Anesthesiology, vol. 75(2), pp. 223-229, (1991).
Streisand et al., "Buccal Absorption of Fentanyl is pH-Dependent in Dogs", Anesthesiology, vol. 82(3), pp. 759-764, Mar. 1995.
Streubel et al., "pH-Independent Release of a Weakly Basic Drug from Water-Insoluble and -Soluble Matrix Tablets", Journal of Controlled Release, vol. 67, pp. 101-110, (2000).
The Alcohol and Other Drug Thesaurus, National Institute of Health, National Institute on Alcohol Abuse and Alcoholics, U.S. Department of Human Services, Third Edition 2000, AOD Thesaurus Annotated Hierarchy: Biomedicine EF EG 16.2, pp. 1-12, Sep. 13, 2004.
Wada, et al., Decision on Appeal 2007-3733, re: U.S. Appl. No. 10/613,220, pp. 1-9, Decided Jan. 14, 2008.
Watson, Notification of Certification of Paragraph IV to Ceph. et al., dated Apr. 15, 2008.
Weatherell et al., "The Flow of Saliva and its Influence on the Movement, Deposition, and Removal of Drugs Administered to the Oral Cavity", Oral Mucosal Drug Delivery, Chptr. 8, pp. 157-187, (1996).
Weinberg et al., "Sublingual Absorption of Selected Opioid Analgesics", Clinical Pharmacology and Therapeutics, vol. 44(3), pp. 335-342, Sep. 1988.
Wertz et al., "Biochemical Basis of the Permeability Barrier in Skin and Oral Mucosa", Oral Mucosal Drug Delivery, Chptr. 2, pp. 27-41, (1996).
Zhang et al., "In Vitro Methods for Measuring Permeability of the Oral Mucosa", Oral Mucosal Drug Delivery, Chptr. 5, pp. 85-97, (1996).
Zhang et al., "Routes of Drug Transport Across Oral Mucosa", Oral Mucosal Drug Delivery, Chptr. 3, pp. 51-61, (1996).
May 2, 2011 Redacted Version of 105 Plaintiff's Reply Brief in Support of Plaintiff's Motion to Stay Proceedings (Attachments #1 Ex. A).
May 2, 2011 Redacted Version of 108 Declaration of Oakes in Support of Plaintiffs Opening Claim Construction Brief by Plaintiffs.
May 2, 2011 Redacted Version of 107 Claim Construction Opening Brief Plaintiff's Opening Claim Construction Brief.
Apr. 27, 2011 Request for Oral Arguments by Sandoz re 88 Motion to Stay Plaintiffs Motion to Stay Proceedings.
Apr. 26, 2011 Request for Oral Arguments by Cephalon et al. re 88 Motion to Stay Plaintiffs Motion to Stay Proceedings.
Apr. 21, 2011 Redacted Version of 98 Answering Brief in Opposition, Part 1 of 3 by Sandoz Inc., (Attachments: # 1 Part 2 of 3, # 2 Part 3 of 3).
2011 *Ceph et al.*, v. *Sandoz* Proposed Order.
Apr. 15, 2011 Joint Claim Construction Chart by Cephalon et al. and Sandoz Inc.
Apr. 14, 2011 Sealed Answering Brief in Opposition re: 88 Motion to Stay Plaintiff's Motion to Stay Proceedings filed by Sandoz Inc. (Attchmnts: # 1 Exh 1-15).
Apr. 11, 2011 *Ceph et al.* v. *Sandoz* Fifth Stipulated Amendment to Scheduling Order.
Apr. 11, 2011 *Ceph et al.* v. *Mylan et al.*, Order for Scheduling Conference.
Apr. 5, 2011 Redacted Version of 96 Letter, to Judge Thynge from Poff regarding Sandoz opposing an extension of pretrial dates requested by Ceph. (ltr dated Mar. 29, 2011).
Apr. 5, 2011 Redacted Version of 92 Letter, to Judge Thynge from Poff regarding Defendant's Response to Plaintiff's Mar. 28, 2011 Letter by Sandoz Inc.
Apr. 5, 2011 Redacted Version of 89 Opening Brief in Support, of Plaintiffs' Motion to Stay Proceedings by Cephalon et al.,(Attachments: # 1 Exhibit A-B).
Search Query of Fentany1.2012.
Mar. 29, 2011 Poff ltr to Thynge re Defendant, Sandoz Response to Plaintiff's 032811 Ltr.
Mar. 29, 2011 Redacted Letter to Thynge (Fish and Richardson) McCann re: Courtesy Copy of Plaintiff's Motion to Stay Action and Opening Brief in anticipation of teleconference.
Mar. 29, 2011 Sandoz Notice of Service of Polli Suppl. and Rebuttal Expert Reports, C.A. No. 10-123-SLR.
Mar. 29, 2011 *Ceph et al.* v. *Mylan et al.*, Document 14 (dated Mar. 29, 2010)Pro Hac Motion and Order for Admission(s) re Figg and Bhatt of Rothwell Figg to represent defendants, Mylan et al., C.A. No. 11-0164-SLR.
Mar. 28, 2011 Letter to Thynge (Fish and Richardson) McCann enclosed courtesy copy of Motion to Stay, Civil Action No. 10-123-SLR-MPT.
Mar. 28, 2011 Sealed Opening Brief in Support re 88 Plaintiff's Motion to Stay, C.A. No. 10-123-SLR/MPT, 18 pp.
Mar. 28, 2011 Plaintiffs Motion to Stay, Proposed Order, C.A. No. 10-123-SLR/MPT.
Mar. 25, 2011 Mylan Answer to Complaint w/ Counterclaim.
Mar. 25, 2011 Plaintiff Notice of Service of Williams Rebuttal Expert Report, C.A. No. 10-123-SLR.
Mar. 25, 2011 Order Setting Discovery Teleconference w/ Thynge, C.A. No. 10-123-SLR/MPT.
Mar. 25, 2011 Mylan Disclosure Statement, C.A. No. 1:11-cv-0164-SLR.
Mar. 25, 2011 Mylan Pharmaceuticals Disclosure Statement, Civil Action No. 1:11-cv-0164 SLR.
Mar. 25, 2011 Substitution of Counsel, Civ. No. 1:11-cv-0164.
Mar. 22, 2011 email re; Order Granting Stipulation to Extend Time.
Mar. 18, 2011 *Ceph et al.* v. *Mylan et al.*, Stipulation to Extend Time to Answer Complaint, Civ. No. 11-164-SLR.
Mar. 17, 2011 Redacted Version 82 Letter, to The Honorable Mary Pat Thynge from John W. Shaw on behalf of Defendant Sandoz Inc. regarding response to Plaintiffs' Mar. 3, 2011 letter to the Court by Sandoz Inc.. (Attachments: # 1 Exhibit A-D)(Keller, Karen) (Entered: Mar. 17, 2011).
Mar. 11, 2011 Order for the transcript of the discussions and rulings during the teleconference of Mar. 11, 2011.

(56) References Cited

OTHER PUBLICATIONS

Mar. 11, 2011 Opinion, *Ceph* v. *Watson*, C.A. No. 08-330-SLR (D. Del. Mar. 11, 2011) (Robinson, J.).
Mar. 3, 2011 Order—Teleconference Transcript Stands as Order of Court re Navinta Discover, C.A. No. 10-123-SLR/MPT.
Mar. 10, 2011 Redacted Sealed Letter to Thynge (Fish & Richardson) Shaw re Plaintiff's Mar. 3, 2011 letter to the Court.
Mar. 10, 2011 Redacted 79 Ltr to Thynge (Fish & Richardson) Marsden re Motion to Compel Discovery by Cephalon et al.—Attchmnt 1-6.
Mar. 8, 2011 Order Setting Teleconference re Discovery Issue, C.A. No. 10-123-SLR/MPT.
Mar. 3, 2011 Sealed Letter to Thynge (Fish & Richardson) Marsden re: pending Motion to Compel Discovery.
Mar. 2, 2011 Executed Summons re Mylan Pharma., served Feb. 25, 2012.
Feb. 28, 2011 Defendant Notice of Service re: Expert Report of Polli, C.A. No. 10-123-SLR.
Feb. 25, 2011 *Ceph et al.* v. *Mylan et al.*, Affidavit of Service from Shinkowsky served on Smith.
Feb. 25, 2011 *Ceph et al.* v. *Sandoz*, Notice of Service Opening Expert Report of Fine, Olsen, and Williams by Cephalon et al.
Feb. 24, 2011 *Ceph et al.* v. *Mylan et al.*, Complaint w/ Exhibits.
Feb. 24, 2011 Report on the Filing or Determination of an Action Regarding a patent or Trademark, C.A. No. 11-CV-164.
Feb. 24, 2011 Supplemental Info. for ANDA Patent Cases.
Feb. 24, 2011 CIMA Disclosure Statement.
Feb. 24, 2011 Cephalon Disclosure Statement.
Feb. 24, 2011 Notice of Availability of Magistrate.
Feb. 24, 2011 Civil Cover Sheet, *Ceph et al.* v. *Mylan et al.*
Feb. 23, 2011 Plaintiffs Notice of Service re Opening Expert Reports, C.A. No. 10-123-SLR.
Feb. 17, 2011 Redacted 72 Ltr to Thynge (Fish and Richardson) Shaw re Motion to Compel the Production of Navinta Formulation and Related Documents by Sandoz.
Feb. 17, 2011 Redacted 67 Ltr to Thynge (Fish and Richardson) Shaw re Discovery Dispute, Attachment #1 Exhibits A-C.
Feb. 16, 2011 Cephalon Notice of Deposition of Jessica Martori, C.A. No. 10-123-SLR.
Feb. 16, 2011 Redacted 66 Ltr to Thynge (Fish and Richardson) Marsden re: Discovery Dispute, Exhibits A-K.
Feb. 15, 2011 Sealed Letter to The Honorable Mary Pat Thynge from John W. Shaw regarding Plaintiffs' Motion to Compel the Production of Navinta Formulation and Related Documents—re 66, Letter, 67 Letter. (Shaw).
Feb. 15, 2011 Redacted Ltr to Thynge (Fish and Richardson) Shaw re Cephalon Motion to Compel Navinta-Related Docs.
Feb. 14, 2011 Order Setting Mediation Conference Mar. 23, 2011, C.A. No. 10-123-SLR.
Feb. 14, 2011 Sandoz Notice of Service re $3^{rd}$ Supplemental Responses and Objections to Cephalon $1^{st}$ Interrogatories, C.A. No. 10-123-SLR.
Feb. 11, 2011 Order Setting Teleconference re Navinta Discovery Issue, C.A. No. 10-123-SLR/MPT.
Feb. 11, 2011 Cephalon Notice of Service re: $3^{rd}$ Supplemental Responses and Objections to Sandoz $1^{st}$ Interrogatories Nos. 1-13.
Feb. 10, 2011 Sealed Letter to Thynge from Shaw regarding Defendant's Objections to Plaintiffs' Motion to Compel re: 66 Letter. (Attachments: #1 Ex. A-C).
Feb. 9, 2011 Redacted Ltr to Thynge (Fish and Richardson) Marsden re: Discovery Dispute.
Feb. 8, 2011 Cephalon et al., Notice of Deposition of Matthew Bohlman on Feb. 28, 2011.
Feb. 8, 2011 Cephalon et al., Notice of Deposition of Suni Vandse on Feb. 15, 2011.
Feb. 3, 2011 Redacted Boyer Declaration in Support of Reply to Motion to Vacate.
Feb. 3, 2011 Redacted Boyer Declaration in Support of Motion to Vacate with Exhibit 1.

Feb. 3, 2011 Redacted *Ceph et al.* v. *Watson et al.* Watson's Reply Brief in Further Support of Its Motion to Vacate the Oct. 28, 2010 Order.
Feb. 2, 2011 Order Setting Teleconference re: Dates for Discovery Issues.
Feb. 2, 2011 Order Setting Teleconference re Dates for Continued Mediation.
Feb. 1, 2011 email to Judge Thynge (Fish & Richardson) Marsden re Parties Availability for Mediation.
Jan. 31, 2011 Order Setting Teleconference to Discuss Feb. 7, 2011 Mediation.
Jan. 28, 2011 Redacted Bradway Declaration in Support of Plaintiffs Opposition to Defendants Motion to Vacate.
Jan. 28, 2011 Redacted Campbell Declaration in Support of Plntffs to Dfndnts Motion to Vacate.
Jan. 28, 2011 Redacted Plaintiffs Opposition to Defendants Motion to Vacate.
Jan. 28, 2011 Redacted Plaintiffs reply in Support of Motion to Strike with Exhibits 1-3.
Jan. 19, 2011 Cephalon Notice of Service re Supplemental Responses-Objections to Sandoz Notice of Deposition, Civil Action No. 10-123-SLR.
Jan. 19, 2011 Text Order Granting $4^{th}$ Stipulated Amendment to Scheduling Order, Civil Action No. 10-123-SLR.
Jan. 19, 2011 Redacted Suzuki Declaration in Support of Motion to Vacate with Exhibits 1-3.
Jan. 19, 2011 Redacted Defendants Motion to Vacate Oct. 28, 2010 Order.
Jan. 18, 2011 Declaration of Gwinn in Support of Watson's Opposition to Ceph et al Motion to Strike Watson's Notice of Subsequent Authority Pursuant to Local Rule 7.1.2(b), or in the Alternative, to Reopen the Record.
Jan. 18, 2011 Watson's Answering Brief in Opposition to Ceph et al. Motion to Strike Watsons' Notice of Subsequent Authority Pursuant to Local Rule 74.1.2(b), or in the Alternative to Reopen the Record.
Jan. 18, 2011 Redacted Suzuki Declaration in Support of Def Answering Brief re Motion to Strike.
Jan. 14, 2011 Fourth Stipulated Amendment to Scheduling Order, Civil Action No. 10-123-SLR.
Jan. 13, 2011 Redacted Booker Declaration in Support of Plaintiffs Motion to Strike.
Jan. 13, 2011 Redacted Defendants Brief in Answering Brief in Opposition to Motion to Strike.
Jan. 13, 2011 Redacted Plaintiffs Brief in Support of Motion to Strike Defendants Not of Subsequent Authority.
Jan. 6, 2011 Signed Protective Order via email.
20110106 Proposed Stipulated Protective Order, Civil Action No. 10-123-SLR.
Dec. 29, 2010 Cephalon Amended Notice of Deposition of Alison Sherwood, Civil Action No. 10-123-SLR.
Dec. 10, 2010 Order Setting Continued Mediation Conference, C.A. No. 10-123-SLR/MPT.
Dec. 6, 2010 Cephalon and CIMA Notice of Service re Responses and Objections to Sandoz $2^{nd}$ Notice of Deposition, Civil Action No. 10-123-SLR.
Dec. 1, 2010 Notice of Service of Sandoz's Objections and Responses to Notice of Rule 30(b)(6) Deposition of Sandoz, Civil Action No. 10-123-SLR.
Nov. 24, 2010 Notice of Service of Responses and Objections of Non-Party Anesta to Sandoz, Inc.'s Subpoena Duces Tecum by Anesta Corp. (McCann).
Nov. 24, 2010 Notice of Service of Responses and Objections of Non-Party Dennis Coleman to Sandoz, Inc.'s Subpoena Ad Testificandum and Duces Tecum by Dennis Coleman, Civil Action No. 10-123-SLR.
Nov. 8, 2011 Redacted Gwinn Declaration in Support of Def Answering Brief re Motion to Strike.
Nov. 18, 2010 Sandoz Notice of Service Objections to Cephalon Subpoena to Navinta, Civil Action No. 10-123-SLR.
Nov. 18, 2010 Sandoz Notice of Subpoenas to Anesta-Coleman-Zhang, Civil Action No. 10-123-SLR.
Nov. 17, 2010 Sandoz Notice of Service Objections to Cephalon Subpoena to Navinta, Civil Action No. 10-123-SLR.

(56) References Cited

OTHER PUBLICATIONS

Nov. 12, 2010 Cephalon Notice of Service re: Supplemental Responses to 1$^{st}$ Set of Interrogatories—Nos. 3 and 5, Civil Action No. 10-123-SLR.
Nov. 5, 2010 Plaintiffs Notice of Service, Civil Action No. 10-123-SLR.
Nov. 1, 2010 Cephalon Notice of Service re: Responses and Objections to Sandoz Notice of Deposition, Civil Action No. 10-123-SLR.
Oct. 29, 2010 Sandoz Notice of Subpoena to Jason Garbell, Civil Action No. 10-123-SLR.
Oct. 29, 2010 Sandoz Notice of Service re: 2$^{nd}$ Notice of Deposition of CIMA and Ceph., Civil Action No. 10-123-SLR.
Oct. 27, 2010 Sandoz Notice of Subpoenas to Univ of WI-Madison, Civ Action No. 10-123-SLR.
Oct. 26, 2010 Sandoz Notice of Subpoenas Duces Tecum and Ad Testificadum on Navinta LLC by CIMA/Cephalon (Compton) Civil Action No. 10-123-SLR.
Oct. 26, 2010 Cephalon Subpoena Executed re: Navinta Civil Action No. 10-123-SLR.
Oct. 26, 2010 Notice of Subpoena, copies of the attached subpoena's directed to Cohen, Millett and Lerner David on Oct. 25, 2010. *Ceph et al.* v. *Sandoz.*
Oct. 26, 2010 Sandoz Notice of Subpoenas to Lerner David, Civil Action No. 10-123-SLR.
Oct. 25, 2010 Cephalon Notice of Deposition of Indranil Nandi, Civil Action No. 10-123-SLR.
Oct. 25, 2010 Cephalon Notice of Deposition of Ellen Camos, Civil Action No. 10-123-SLR.
Oct. 25, 2010 Cephalon Notice of Deposition of Allison Sherwood, Civil Action No. 10-123-SLR.
Oct. 25, 2010 Order Setting Mediation Conference, C.A. No. 10-123-SLR/MPT, *Ceph et al.* v. *Sandoz.*
Oct. 18, 2010 Cephalon Notice of Deposition to Sandoz, Civil Action No. 10-123-SLR.
Oct. 18, 2010 Sandoz Notice of Service, Civil Action No. 10-123-SLR.
Oct. 13, 2010 Sandoz Notice of Service re: Responses and Objections to Cephalon 1$^{st}$ Interrogatories and Request for Production of Documents, Civil Action No. 10-123-SLR.
Oct. 12, 2010 Cephalon Notice of Service re: Responses and Objections to Sandoz 1$^{st}$ Interrogatories and Request for Production of Documents, Civil Action No. 10-123-SLR.
Oct. 5, 2010 Text Order Granting Stipulated Amendment to Scheduling Order via Email.
Oct. 1, 2010 Stipulated Amendment to SO re: Doc Production and Claim Terms Exchange, Civil Action No. 10-123-SLR. *Ceph et al.* v. *Sandoz.*
Sep. 22, 2010 Order Setting Teleconference with MJ Thynge, C.A. No. 10-123-SLR.
Sep. 10, 2010 Redacted Corrected Watson Reply Post Trial Brief.
Sep. 1, 2010 Cephalon Notice of Entry of Appearance of Compton (FR), Civil Action No. 10-123-SLR. *Ceph et al.* v. *Sandoz.*
Aug. 31, 2010 Redacted Booker Declaration in Support of Reply Post Trial Brief with Ex. 1 and 2.
Aug. 31, 2010 Order Scheduling ADR Teleconference—Sep. 22, 2010, CA 10-123-SLR/MPT.
Aug. 31, 2010 Sandoz Notice of Service re 1$^{st}$ Set interrogatories and Request for Production of Documents to Sandoz.
Aug. 30, 2010 2$^{nd}$ Stipulated Amendment to Scheduling Order re: Doc Production, Civil Action No. 10-123-SLR. *Ceph et al.* v. *Sandoz.*
Aug. 30, 2010 Cephalon Notice of Service re: 1$^{st}$ Set Interrogatories and Request for Production of Documents to Sandoz.
Aug. 16, 2010 Redacted Booker Declaration in Support of Opposition to Motion to Strike with Ex. A & B.
Aug. 16, 2010 *Ceph et al.*, v. *Watson et al.*, Plaintiffs' Brief in Opposition to Defendants' Motion to Strike Expert Testimony.
Aug. 13, 2010 Booker Declaration in Support of Ceph et al, Post Trial Reply Brief on Infringement.
Aug. 13, 2010 Redacted Post-trial Brief of Watson—Document 273—filed Aug. 20, 2010.
Aug. 13, 2010 Redacted Plaintiffs Reply Post-Trial Brief—Corrected.
Aug. 13, 2010 Order Rescheduling ADR Teleconference, C.A. No. 10-123-SLR/MPT.
Aug. 12, 2010 Order Scheduling ADR Teleconference—Sep. 22, 2010, C.A. No. 10-123-SLR/MPT.
Aug. 11, 2010 Redacted Declaration of Bryan Braunel re Motion to Strike Exp Testimony.
Aug. 10, 2010 Redacted Plaintiffs Opposition to Motion to Strike.
Aug. 5, 2010 Order Scheduling ADR Teleconference, C.A. No. 10-123-SLR/MPT.
Aug. 5, 2010 Order Regarding Discovery Matter, C.A. No. 10-123-SLR/MPT. *Ceph et al.* v. *Sandoz.*
Jul. 30, 2010 Redacted Defendants Responsive Post-Trial Brief.
Jul. 30, 2010 Redacted Watson Motion to Strike Expert Testimony.
Jul. 30, 2010 Plaintiffs Responsive Post-Trial Brief on Validity.
Jul. 29, 2010 Stipulated Amendment to Scheduling Order re: Doc Production, C.A. No. 10-123-SLR. *Ceph et al.* v. *Sandoz.*
Jul. 20, 2010 Order Scheduling ADR Teleconference, C.A. No. 10-123-SLR-LPS. *Ceph et al.* v. *Sandoz.*
Jun. 29, 2010 Redacted Watson Opening Post-Trial Brief.
Jun. 29, 2010 Redacted plaintiffs Opening Post-Trial Brief.
Jun. 3, 2010 Scheduling Order Entered via email. *Ceph et al.* v. *Sandoz.*
Jun. 3, 2010 Order Regarding Discovery Matters, C.A. No. 10-123-SLR-LPS.
May 25, 2010 Notice of Service re: Defendants Initial Disclosures, Civil Action No. 10-123-SLR. *Ceph et al.* v. *Sandoz.*
May 25, 2010 Notice of Service re Plaintiffs Initial Disclosures, Civil Action No. 10-330-SLR. *Ceph et al.* v. *Sandoz.*
May 24, 2010 Order re: Teleconference—via email. *Ceph et al.* v. *Mylan et al.*
May 20, 2010 Final Proposed Scheduling Order, C.A. No. 10-123-SLR. *Ceph et al.* v. *Sandoz.*
May 11, 2010 Order Regarding Teleconference—Court Docket Error, to Watson and Barr from Doug McCann.
May 11, 2010 Proposed Scheduling Order, C.A. No. 10-123-SLR. *Ceph et al.* v. *Sandoz.*
Apr. 27, 2010 Telephone conversation dated Apr. 19, 2010, Apr. 20, 2010 and Apr. 21, 2010 re: 04815716.8 for auxiliary.
Apr. 26, 2010 Redacted Pretrial Order, Civil Action No. 08-330-SLR.
Apr. 23, 2010 Redacted Plaintiff's Brief in Opposition to Defendants Motion to Exclude Certain $CO_2$ Testing, C.A. No. 08-330-SLR.
Apr. 20, 2010 Booker Declaration in Support of Motion Responsive Post-Trial Brief on Validity—Exhibits 1-5.
Apr. 20, 2010 Deposition of Stephen R. Byrne.
Apr. 20, 2010 Order Setting Scheduling Teleconference. *Ceph et al.* v. *Sandoz.*
Apr. 19, 2010 *Ceph et al.* v. *Watson et al.*, Proposed Joint Pretrial Order.
Apr. 15, 2010 Answer to Counterclaims, Civil Action No. 10-330-SLR. *Ceph et al.* v. *Sandoz.*
Apr. 9, 2010 Redacted Watson Motion to Exclude $CO_2$ Testing.
Apr. 1, 2010 Redacted Cephalon Reply in Support of Motion to Modify Protective Orders.
Mar. 31, 2010 Text Order re: Pro Hac Admission of McDermott Attorneys for Sandoz vial email.
Mar. 30, 2010 *Ceph et al.* v. *Watson et al.*, Defendant's Answering Claim Construction Brief.
Mar. 30, 2010 Redacted Cephalon Marksman Brief.
Mar. 30, 2010 Redacted Watson Pharma Rebuttal Marksman Brief.
Mar. 24, 2010 So Ordered—re 10 Motion for Pro Hac Vice Appearance of Attorney Jeffrey R. Gargano. Signed by Judge Sue L. Robinson on Mar. 24, 2010. (lid) (Entered: Mar. 24, 2010).
Mar. 23, 2010 Sandoz Pro Hac Vice Motion—Garcha-Dolkas-Chang-Boyle of McDermott, C.A. No. 10-00123-SLR.
Mar. 22, 2010 Sandoz Answer, Defense, Counterclaims, C.A. No. 10-00123-SLR.
Mar. 22, 2010 Sandoz Inc's Rule 7.1 Disclosure Statement, C.A. No. 10-00123-SLR.
Mar. 22, 2010 Sandoz Pro HacVice Motion and Order—Gargano of McDermott.

(56) References Cited

OTHER PUBLICATIONS

Mar. 15, 2010 Redacted Watson Answering Brief in Opposition of Motion to Modify Protective Orders.
Mar. 11, 2010 Text Order Granting Stipulation to Extend Time to Answer. *Ceph et al. v. Sandoz*.
Mar. 10, 2010 Stipulation and Order to Extend Time re: Answer to Complaint. *Ceph et al. v. Sandoz*.
Mar. 5, 2010 *Ceph. v. Watson*, Watson Opening Claim Construction Brief.
Mar. 5, 2010 Redacted Fineman Declaration in Support of Watson Opening Claim Brief.
Mar. 5, 2010 Redacted Plaintiffs Consolidated Opening Marksman Brief.
Feb. 22, 2010 Summons Executed by Cephalon Inc., CIMA Labs Inc. Sandoz Inc. served on Feb. 17, 2010. (Marsden).
Feb. 17, 2010 Report on the Filing or Determination of an Action Regarding a Patent or Trademark, C.A. No. 10-cv-00123-UNA. *Ceph et al. v. Sandoz*.
Feb. 17, 2010 Sandoz Summons in a Civil Action.
Feb. 17, 2010 Proof of Service, US District Court for the District of Delaware.
Feb. 16, 2010 *Ceph et al., v. Sandoz*, Civil Cover.
Feb. 16, 2010 *Ceph et al., v. Sandoz*, Complaint.
Feb. 16, 2010 *Ceph et al., v. Sandoz*, Exhibit A—'604 Patent Submitted with Complaint.
Feb. 16, 2010 *Ceph et al., v. Sandoz*, Exhibit B—'590 Patent Submitted with Complaint.
Feb. 16, 2010 Cephalon Corporate Disclosure Statement Pursuant to Rule 7.1 of the Fed. Rules of CIV. Procedure.
Feb. 16, 2010 CIMA Corporate Disclosure Statement Pursuant to Rule 7.1 of the Fed. Rules of CIV. Procedure.
Feb. 16, 2010 Notice Consent and Reference to a Magistrate, C.A. No. 10-CV-00123-UNA.
Feb. 12, 2010 Joint Claim Construction, *Ceph et al. v. Watson et al.*
May 29, 2009 *Ceph et al. v. Barr et al.*, Plaintiffs' Second Set of Interrogatories (Nos. 1-10) Civil Action No. 08-455-SLR.
May 18, 2009 *Ceph et al. v. Watson et al.*, Answer to Counterclaims.
May 29, 2009 *Ceph et al. v. Watson et al.*, Defendant's Second Supplemental Objections and Responses to Plaintiffs' First Set of Interrogatories.
Apr. 29, 2009 *Ceph et al. v. Watson et al.*, Response to Defendants' Invalidity Contentions, Civil Action No. 08-330-SLR.
Apr. 27, 2009 *Ceph et al. v. Watson et al.*, Answer and Counterclaims.
Apr. 3, 2009 Order Denying Motion to Dismiss, C.A. No. 08-330-SLR, *Ceph et al. v. Watson et al.*
Apr. 1, 2009 Redacted Park Declaration in Support of Watson Reply in Support of Motion to Dismiss Amended Complaint, C.A. No. 08-CV-00330-SLR.
Apr. 1, 2009 Redacted Watson et al., Reply Brief in Support of Motion to Dismiss—Amended Complaint, C.A. No. 08-330-SLR.
Mar. 30, 2009 *Ceph et al. v Watson*, Defendant's Supplemental Objections and Responses to Plaintiffs' First Set of Interrogatories, C.A. No. 08-330-SLR.
Mar. 30, 2009 *Ceph et al. v. Barr et al.*, Plaintiff's Supplemental Response to Defendants' First Set of Interrogatories (Nos. 1-10).
Mar. 29, 2011 Fish & Richardson Redacted Letter to Thynge (McCann) re Discovery Extension—Proposed Order C.A. No. 10-123-SLR/MPT.
Mar. 29, 2011 Fish & Richardson Later to Thynge, *Ceph et al. v. Sandoz* re: teleconference for Plaintiff's Motion to Stay Action and Opening Brief.
Mar. 28, 2011 Fish & Richardson Letter to Thynge enclosing courtesy copy of Motion to Stay.
Mar. 23, 2009 Oakes Declaration in Support of Opposition to Watson Pharma., Motion to Dismiss Amended Complaint, C.A. No. 08-330-SLR.
Mar. 23, 2009 Redacted Brief in Opposition to Watson et al., Motion to Dismiss, C.A. No. 08-330-SLR.
Mar. 16, 2009 Declaration of Robert M. Oakes in Support of Plaintiff's Brief in Opposition to Watson Pharma, Motion to Dismiss Counts 1, 2, 4 and 5 of the Amended Complaint Pursuant to Fed. R. Civ. P. 12(B)(6)(7); and Defendants' Motion to Dismiss Counts 3 and 6 of the Amended Complaint Pursuant to FED. R. CIV. P. 12(B)(1).
Mar. 16, 2009 Ceph et al. Brief in Opposition to Watson Pharma's Motion to Dismiss Counts 1, 2, 4, and 5 of the Amended Complaint Pursuant to FED. R. CIV. P. 12(B)(6) and (7); and Defendants's Motion to Dismiss Counts 3 and 6 of the Amended Complaint Pursuant to Fed. R. Civ. P. 12(B)(1).
Mar. 13, 2009 *Ceph et al. v. Barr et al.*, Answer to Counterclaims, Civil Action No. 09-074 SLR.
Feb. 23, 2009 *Ceph et al. v. Barr Pharma et al.*, Answer, Affirmative Defenses and Counterclaims, Case No. 1:09-cv-00074-SLR.
Feb. 20, 2009 Redacted Watson Labs Reply Brief in Support of Motion to Dismiss.
Feb. 20, 2009 Redacted Watson Pharma Reply Brief in Support of Motion to Dismiss, C.A. No. 08-330-SLR.
Feb. 20, 2009 Redacted Declaration of Park in Support of Watsons' Motion to Dismiss Counts 1, 2, 4, and 5 of The Amended Complaint and Watson's Opening Brief in Support of Their Motion to Dismiss Counts 3 and 6 of the Amended Complaint—Exhibits 1-30.
Feb. 20, 2009 Redacted Watson Defendants Opening Brief in Support of Motion to Dismiss Amended Complaint, C.A. No. 08-330-SLR.
Feb. 17, 2009 *Ceph et al. v. Barr et al.*, Answer to Counterclaims.
Feb. 11, 2009 *Ceph et al. v. Barr et al.*, Responses and Objections to Ceph et al. Second Set of Interrogatories (No. 11), Case No. 08-cv-00455 (SLR).
Feb. 4, 2009 *Ceph et al. v. Watson et al.* Amended Complaint for Patent Infringement, Civil Action No. 08-330 SLR (Redacted).
Jan. 30. 2009 *Ceph et al. v. Barr et al.*, Complaint for Patent Infringement.
Jan. 27, 2009 *Ceph et al. v. Barr et al.*, Answer, Affirmative Defenses and Counterclaims, Case No. 08-cv-810 SLR.
Jan. 26, 2009 *Ceph et al. v. Watson et al.*, Plaintiffs Responses to Defendants First Set of Interrogatories, (Nos. 1-10) Civil Action No. 08-455-SLR.
Jan. 16, 2009 *Ceph et al. v. Watson et al.* Amended Complaint for Patent Infringement.
Jan. 12, 2009 *Ceph et al. v. Watson et al.*, Defendant's Objections and Responses to First Set of Interrogatories, (No. 1-11), Case No. 08-330-SLR.
Jan. 9, 2009, *Ceph et al. v. Barr Pharma et al.*, Barr's Responses and Objection to Ceph et al., First Set of Interrogatories (No. 1-10).
Dec. 23, 2008, *Ceph et al. v. Barr et al.*, Barr's First Set of Interrogatories to Ceph et al., (Nos. 1-10), Case No. 08pcv-00455 (JJF).
Nov. 3, 2008, *Ceph et al. v. Watson et al.*, Answer to Counterclaims, Case No. 3:08-cv-00308-LHR-RAM.
Oct. 29, 2008 *Ceph et al. v. Barr et al.*, Complaint for Patent Infringement.
Oct. 14, 2008 *Ceph et al. v. Watson et al.*, Answer and Counterclaims, Case No. 3:08-CV-308-LRH-RAM.
Sep. 18, 2008, *Ceph et al., v. Watson et al.*, Defendants First Set of Rule 33 Interrogatories to Plntiffs, Case No. 08-330-JJF.
Sep. 17, 2008, Stern Kessler Letter.
Sep. 4, 2008 *Ceph et al. v. Barr et al.*, Answer to Counterclaims.
Aug. 12, 2008 *Ceph et al., v. Barr et al.*, Answer, Affirmative Defenses and Counterclaims, pp. 1-18.
Jul. 22, 2008 Redacted Watson Pharma Opening Brief in Support of Motion to Dismiss, Case No. 08-330-JJF.
Jul. 22, 2008 *Ceph et al. v. Barr et al.*, Complaint for Patent Infringement.
Jul. 22, 2008 Redacted Watson Lab Opening Brief in Support of Motion to Dismiss, Case No. 08-330-JJF.
Jul. 15, 2008 Watson Labs Motion to Dismiss Pursuant to Fe. R. Civ. P. 12(b)(6) and (7), Case No. 08-330-JJF.
Jul. 15, 2008 Watson Pharmaceuticals Motion to Dismiss Pursuant to Fed. R. Civ. P. 12(b)(6) and (7).
Jun. 3, 2008 *Ceph et al. v. Watson et al.* Complaint for Patent Infringement.
Jun. 2, 2008 Report of Filing an Action, Docket No. 08-cv-330.
Apr. 15, 2008 Watson ltr re: Notification of Certification of Invalidity, Unenforceability and/or Non-Infringement for U.S.

* cited by examiner

SUBLINGUAL BUCCAL EFFERVESCENT

CROSS-REFERENCE TO RELATED APPLICATION

The present application is a Continuation Application of U.S. patent application Ser. No. 12/429,475, filed Apr. 24, 2009, which is a Continuation of U.S. patent application Ser. No. 09/661,693, filed Sep. 14, 2000, now abandoned, which is a Continuation Application of U.S. patent application Ser. No. 09/327,814 filed Jun. 8, 1999, now patented as U.S. Pat. No. 6,200,604, which is a Continuation Application of U.S. patent application Ser. No. 09/277,424, filed Mar. 26, 1999, now abandoned, which claims the benefit of U.S. Provisional Application No. 60/079,652 filed on Mar. 27, 1998, now expired, the disclosures of which are herein incorporated by reference in their entirety.

The present application is also related to U.S. Pat. No. 6,974,590, U.S. patent application Ser. No. 10/269,669, filed Oct. 11, 2002, U.S. patent application Ser. No. 10/977,029 filed Oct. 29, 2004 and U.S. patent application Ser. No. 11/511,098, filed Aug. 28, 2006, the disclosures of which are herein incorporated by reference.

FIELD OF THE INVENTION

The present invention relates to pharmaceutical compositions, and more particularly to pharmaceutical compositions for oral administration of a medicament, which contain an effervescent agent for enhancing oral drug absorption across the buccal, sublingual, and gingival mucosa.

DESCRIPTION OF PRIOR ART

Effervescents have been shown to be useful and advantageous for oral administration. See Pharmaceutical Dosage Forms: Tablets Volume I, Second Edition. A. Lieberman. ed. 1989, Marcel Dekker, Inc. As discussed in this text, and as commonly employed, an effervescent tablet is dissolved in water to provide a carbonated or sparkling liquid drink. See also U.S. Pat. Nos. 5,102,665 and 5,468,504 to Schaeffer, herein incorporated by reference. In such a drink, the effervescent helps to mask the taste of medicaments.

Effervescent compositions have also been employed for use as taste masking agents in dosage forms which are not dissolved in water prior to administration. For example, U.S. Pat. No. 4,639,368 describes a chewing gum containing a medicament capable of absorption through the buccal cavity and containing a taste masking amount of an effervescent.

More recently effervescents have been employed to obtain rapid dissolution and/or dispersion of the medicament in the oral cavity. See U.S. Pat. Nos. 5,178,878 and 5,223,264. The effervescent tends to stimulate saliva production thereby providing additional water to aid in further effervescent to a faster onset of action and/or improved bioavailability action. These dosage forms give an agreeable presentation of the drug, particularly for patients who have difficulty in swallowing tablets or capsules. PCT application WO 97/06786 describes pre-gastric absorption of certain drugs using rapidly-disbursing dosage forms.

Various proposals have been advanced for oral mucosal administration of various drugs. When drugs are absorbed from the oral mucosa, they bypass the gastrointestinal and hepatic metabolism process. This can lead of a drug. However, many compounds do not rapidly penetrate the oral mucosa. See, e.g., Christina Graffner, Clinical Experience with Novel Buccal and Sublingual Administration; NOVEL DRUG DELIVERY AND ITS THERAPEUTIC APPLICATION, edited by L. F. Prescott and W. S. Nimmo (1989); David Harris & Joseph R. Robinson, Drug Delivery via the Mucous Membranes of the Oral Cavity; JOURNAL OF PHARMACEUTICAL SCIENCES, Vol. 81 (January 1992); Oral Mucosal Delivery, edited by M. J. Rathbone, which are herein incorporated by reference. The compounds which may be well absorbed per-orally (through the gastrointestinal tract) may not be well absorbed through the mucosa of the mouth because the oral mucosa is less permeable than the intestinal mucosa and it does not offer as big a surface area as the small intestine.

Despite these and other efforts toward increasing the permeation of medicaments across the oral mucosa, there have been unmet needs for improved methods of administrating medicaments across the oral mucosa.

SUMMARY OF THE INVENTION

The pharmaceutical compositions of the present invention comprise an orally administrable medicament in combination with an effervescent agent used as penetration enhancer to influence the permeability of the medicament across the buccal, sublingual, and gingival mucosa.

DETAILED DESCRIPTION OF THE INVENTION

One aspect of this invention is to use effervescent as penetration enhancers for influencing oral drug absorption. Effervescent agents can be used alone or in combination with other penetration enhancers, which leads to an increase in the rate and extent of absorption of an active drug. It is believed that such increase can rise from one or all of the following mechanisms:

1. reducing the mucosal layer thickness and/or viscosity;
2. tight junction alteration;
3. inducing a change in the cell membrane structure; and
4. increasing the hydrophobic environment within the cellular membrane.

The present dosage forms should include an amount of an effervescent agent effective to aid in penetration of the drug across the oral mucosa. Preferably, the effervescent is provided in an amount of between about 5% and about 95% by weight, based on the weight of the finished tablet, and more preferably in an amount of between about 30% and about 80% by weight. It is particularly preferred that sufficient effervescent material be provided such that the evolved gas is more than about 5 cm.sup.3 but less than about 30 cm.sup.3, upon exposure of the tablet to an aqueous environment. However, the amount of effervescent agent must be optimized for each specific drug.

The term "effervescent agent" includes compounds which evolve gas. The preferred effervescent agents evolve gas by means of a chemical reaction which takes place upon exposure of the effervescent agent (an effervescent couple) to water and/or to saliva in the mouth. This reaction is most often the result of the reaction of a soluble acid source and a source of carbon dioxide such as an alkaline carbonate or bicarbonate. The reaction of these two general compounds produces carbon dioxide gas upon contact with water or saliva. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included.

The effervescent agent(s) of the present invention is not always based upon reaction which forms carbon dioxide. Reactants which evolve oxygen or other gasses which are safe for human consumption are also considered within the scope. Where the effervescent agent includes two mutually reactive components, such as an acid source and a carbonate source, it is preferred that both components react completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, in other embodiments of the present invention, the amount of either acid or carbonate source may exceed the amount of the other component. This may be useful to enhance taste and/or performance of a tablet containing an overage of either component. In this case, it is acceptable that the additional amount of either component may remain unreacted.

The present dosage forms may also include in amounts additional to that required for effervescence a pH adjusting substance. For drugs that are weakly acidic or weakly basic, the pH of the aqueous environment can influence the relative concentrations of the ionized and unionized forms of the drug present in solution according to the Henderson-Hasselbach equation. The pH solutions in which an effervescent couple has dissolved is slightly acidic due to the evolution of carbon dioxide. The pH of the local environment, e.g., saliva in immediate contact with the tablet and any drug that may have dissolved from it, may be adjusted by incorporating in the tablet a pH adjusting substances which permit the relative portions of the ionized and unionized forms of the drug to be controlled. In this way, the present dosage forms can be optimized for each specific drug. If the unionized drug is known or suspected to be absorbed through the cell membrane (transcellular absorption) it would be preferable to alter the pH of the local environment (within the limits tolerable to the subject) to a level that favors the unionized form of the drug. Conversely, if the ionized form is more readily dissolved the local environment should favor ionization.

The aqueous solubility of the drug should preferably not be compromised by the effervescent and pH adjusting substance, such that the dosage forms permit a sufficient concentration of the drug to be present in the unionized form. The percentage of the pH adjusting substance and/or effervescent should therefore be adjusted depending on the drug.

Suitable pH adjusting substance for use in the present invention include any weak acid or weak base in amounts additional to that required for the effervescence or, preferably, any buffer system that is not harmful to the oral mucosa. Suitable pH adjusting substance for use in the present invention include, but are not limited to, any of the acids or bases previously mentioned as effervescent compounds, disodium hydrogen phosphate, sodium dihydrogen phosphate and the equivalent potassium salt.

The active ingredient suitable for use in the present dosage forms can include systematically distributable pharmaceutical ingredients, vitamins, minerals, dietary supplements, as well as non-systematically distributable drugs. Preferably, the active ingredient is a systemically active pharmaceutical ingredient which is absorbable by the body through the oral mucosa. Although the dosage forms can be employed with a wide range of drugs, as discussed below, it is especially suitable for drugs and other pharmaceutical ingredients which suffer significant loss of activity in the lumen of the gastrointestinal tract or in the tissues of the gastrointestinal tract during absorption process or upon passage through the liver after absorption in the intestinal tract. Absorption through the oral mucosa allows the drug to enter the systemic circulation without first passing through the liver, and thus alleviates the loss of activity upon passage through the liver.

Pharmaceutical ingredients may include, without limitation, analgesics, anti-inflammatories, antipyretics, antibiotics, antimicrobials, laxatives, anorexics, antihistamines, antiasthmatics, antidiuretics, antiflatulents, antimigraine agents, antispasmodics, sedatives, antihyperactives, antihypertensives, tranquilizers, decongestants, beta blockers; peptides, proteins, oligonucleotides and other substances of biological origin, and combinations thereof. Also encompassed by the terms "active ingredient(s)", "pharmaceutical ingredient(s)" and "active agents" are the drugs and pharmaceutically active ingredients described in Mantelle, U.S. Pat. No. 5,234,957, in columns 18 through 21. That text of Mantelle is hereby incorporated by reference. Alternatively or additionally, the active ingredient can include drugs and other pharmaceutical ingredients, vitamins, minerals and dietary supplements as the same are defined in U.S. Pat. No. 5,178,878, the disclosure of which is also incorporated by reference herein.

The dosage form preferably includes an effervescent couple, in combination with the other ingredients to enhance the absorption of the pharmaceutical ingredient across the oral mucosa and to improve the disintegration profile and the organoleptic properties of the dosage form. For example, the area of contact between the dosage form and the oral mucosa, and the residence time of the dosage form in the oral cavity can be improved by including a bioadhesive polymer in this drug delivery system. See, e.g., Mechanistic Studies on Effervescent-Induced Permeability Enhancement by Jonathan Eichman (1997), which is incorporated by reference herein. Effervescence, due to its mucus stripping properties, would also enhance the residence time of the bioadhesive, thereby increasing the residence time for the drug absorption. Non-limiting examples of bioadhesives used in the present invention include, for example, Carbopol 934 P, Na CMC, Methocel, Polycarbophil (Noveon AA-1), HPMC, Na alginate, Na Hyaluronate and other natural or synthetic bioadhesives.

In addition to the effervescence-producing agents, a dosage form according to the present invention may also include suitable non-effervescent disintegration agents. Non-limiting examples of non-effervescent disintegration agents include: microcrystalline, cellulose, croscarmellose sodium, crospovidone, starches, corn starch, potato starch and modified starches thereof, sweeteners, clays, such as bentonite, alginates, gums such as agar, guar, locust bean, karaya, pecitin and tragacanth. Disintegrants may comprise up to about 20 weight percent and preferably between about 2 and about 10% of the total weight of the composition.

In addition to the particles in accordance with the present invention, the dosage forms may also include glidants, lubricants, binders, sweeteners, flavoring and coloring components. Any conventional sweetener or flavoring component may be used. Combinations of sweeteners, flavoring components, or sweeteners and flavoring components may likewise be used.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. Binders may be used in an amount of up to 60 weight percent and preferably about 10 to about 40 weight percent of the total composition.

Coloring agents may include titanium dioxide, and dyes suitable for food such as those known as FD&C dyes and natural coloring agents such as grape skin extract, beet red powder, beta-carotene, annato, carmine, turmeric, paprika, etc. The amount of coloring used may range from about 0.1 to about 3.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.05 to about 3 percent by weight based upon the weight of the composition. Particularly preferred flavors are the grape and cherry flavors and citrus flavors such as orange.

One aspect of the invention provides a solid, oral tablet dosage form suitable for sublingual, buccal, and gingival administration. Excipient fillers can be used to facilitate tableting. The filler desirably will also assist in the rapid dissolution of the dosage form in the mouth. Non-limiting examples of suitable fillers include: mannitol, dextrose, lactose, sucrose, and calcium carbonate.

Method of Manufacture

Tablets can either be manufactured by direct compression, wet granulation or any other tablet manufacturing technique. See, e.g., U.S. Pat. Nos. 5,178,878 and 5,223,264, which are incorporated by reference herein. The tablet may be a layered tablet consisting of a layer of the active ingredient sandwiched between a bioadhesive layer and an effervescence layer. Other layered forms which include the ingredients set forth above in layers of diverse compositions.

Effervescence Level: Between 5%-95%
Tablet size: Between 3/16"-5/8"
Tablet hardness: Between 5N and 80N
Route of administration: Sublingual, Buccal, Gingival The dosage form may be administered to a human or other mammalian subject by placing the dosage form in the subject's mouth and holding it in the mouth, either adjacent a cheek (for buccal administration), beneath the tongue (for sublingual administration) and between the upper lip and gum (for gingival administration). The dosage form spontaneously begins to disintegrate due to the moisture in the mouth. The disintegration, and particularly the effervescence, stimulates additional salivation which further enhances disintegration.

Example 1

The dosage form should include Fentanyl, an effervescent and pH adjusting substance so that the pH is adjusted to neutral (or slightly higher) since the pKa of fentanyl is 7.3. At this pH, the aqueous solubility of this poorly water-soluble drug would not be compromised unduly, and would permit a sufficient concentration of the drug to be present in the unionized form.

Two fentanyl formulations, each containing 36% effervescence, were produced. These tablets were compressed using half-inch shallow concave punches.

| FORMULATION | COMPONENT | QUANTITY (MG) |
|---|---|---|
| SHORT DISINTEGRATION TIME | Fentanyl, citrate, USP | 1.57 |
| | Lactose monohydrate | 119.47 |
| | MicrocrystallineCellulose, Silicified | 119.47 |
| | Sodium bicarbonate anhydrous | 46.99 |
| | Citric acid, anhydrous | 105 |
| | Polyvinylphrrolidone, cross-linked | 75 |
| | Magnesium stearate | 25 |
| | Colloidal silicon dioxide | 2.5 |
| | Total tablet mass | 500 |
| LONG DISINTEGRATION TIME | Fentanyl citrate, USP | 1.57 |
| | Lactose Monohydrate | 270.93 |
| | Sodium carbonate, anhydrous | 40.00 |
| | Sodium bicarbonate | 105 |
| | Citric acid, anhydrous | 75 |
| | Magnesium stearate | 5 |
| | Colloidal silicon dioxide | 2.5 |
| | Total tablet mass | 500 |

The dosage form included prochlorperazine (pKa=8.1), an effervescent and pH adjusting substance so that a slightly higher pH is produced to facilitate the permeation enhancement.

With respect to prochlorperazine, an anti-emetic drug, two formulations, buccal and sublingual, were developed. The buccal tablets were compressed as quarter inch diameter biconvex tablets, whereas the sublingual tablets were three-eighths inch diameter biconvex tablets. These dimensions were chosen to give a comfortable fit in the respective part of the oral cavity for which they were designed. The formulae for these tablets are as follows:

Example 2

| FORMULATION | COMPONENT NAME | QUANTITY (MG) |
|---|---|---|
| BUCCAL | Phrochlorperazine | 5.00 |
| | Sodium Bicarbonate | 15.52 |
| | Citric Acid, Anhydrous | 11.08 |
| | Sodium Bicarbonate | 45.78 |
| | HPMCK4M Prem | 5.00 |
| | Dicalcium phosphate dihydrate | 5.00 |
| | Mannitol | 11.67 |
| | Magnesium Stearate | 0.95 |
| | TOTAL | 100.00 |
| SUBLINGUAL | Phrochlorperazine | 5.00 |
| | Sodium Bicarbonate | 61.25 |
| | Citric Acid, Anhydrous | 43.75 |
| | Sodium Bicarbonate | 95 |
| | Sodium carbonate | 91.25 |
| | HPMC Methocel K4M Prem | 40 |
| | Mannitol | 60 |
| | Magnesium Stearate | 3.75 |
| | TOTAL | 400 |

The invention claimed is:

1. A method of administering at least one systemically distributable pharmaceutical agent across the oral mucosa comprising:
   a) providing a solid oral dosage form including:
      (1) an orally administerable medicament that is present in an amount that is pharmaceutically effective for buccal mucosal, gingival, or sublingual mucosal administration;
      (2) at least one pH adjusting substance, which is a base selected from sodium carbonate, potassium carbonate, magnesium carbonate, disodium hydrogen phosphate, sodium dihydrogen phosphate, dipotassium hydrogen phosphate, and potassium dihydrogen phosphate; and
      (3) at least one saliva activated effervescent couple in an amount sufficient to increase absorption of said orally administerable medicament across the oral mucosa, wherein said effervescent couple comprises an acid selected from citric, tartaric, malic, fumaric, adipic and succinic acid, and a base selected from sodium bicarbonate, sodium carbonate, potassium bicarbonate, potassium carbonate, and magnesium carbonate; wherein said orally administerable medicament is not substantially encompassed by or dispersed in a material that prevents absorption of said medicament across the oral mucosa;
   b) placing said solid oral dosage form in the mouth of a patient so that saliva in said patient's mouth activates said at least one effervescent couple in said tablet; and
   c) holding said solid oral dosage form and dissolving the contents of said solid oral dosage form in the mouth of a patient whereby said at least one effervescent couple promotes absorption of said orally administerable medicament across the oral mucosa.

2. The method of administering at least one systemically distributable pharmaceutical agent according to claim 1 wherein said step c) includes holding said solid oral dosage form and dissolving the contents of said solid oral dosage form in said mouth adjacent a cheek for buccal administration.

3. The method of administering at least one systemically distributable pharmaceutical agent according to claim 1 wherein said step c) includes holding said solid oral dosage form and dissolving the contents of said solid oral dosage form in said mouth beneath the tongue for sublingual administration.

4. The method of administering at least one systemically distributable pharmaceutical agent according to claim 1 wherein said step c) includes holding said solid oral dosage form and dissolving the contents of said solid oral dosage form in said mouth between the upper lip and gum for gingival administration.

5. The method of administering at least one systemically distributable pharmaceutical agent according to claim 1, wherein said solid oral dosage form further includes a bioadhesive, wherein said bioadhesive increases the contact time between said solid oral dosage form and the oral mucosa.

6. The method of administering at least one systemically distributable pharmaceutical agent according to claim 1, wherein said solid oral dosage form further includes glidants, lubricants, binders, sweeteners, flavoring and coloring components.

7. The method of administering at least one systemically distributable pharmaceutical agent according to claim 1, wherein said orally administerable medicament is selected from the group consisting of analgesics, anti-inflammatories, antipyretics, antibiotics, antimicrobials, laxatives, anorexics, antihistamines, antiasthmatics, antidiuretics, antiflatuents, anti-emetics, antimigraine agents, antispasmodics, sedatives, antihyperactives, antihypertensives, tranquilizers, decongestants, and beta blockers.

8. The method of administering at least one systemically distributable pharmaceutical agent according to claim 1, wherein said orally administerable medicament is selected from the group consisting of peptides, proteins and oligonucleotides.

9. The method of administering at least one systemically distributable pharmaceutical agent according to claim 1, wherein said at least one effervescent couple is present in an amount between about 5% by weight and 95% by weight.

10. The method of administering at least one systemically distributable pharmaceutical agent according to claim 1, wherein said at least one effervescent couple is present in an amount between about 30% by weight and 80% by weight.

11. The method of administering at least one systemically distributable pharmaceutical agent according to claim 1, wherein said at least one effervescent couple is present in an amount sufficient to evolve a gas in an amount between about 5 cm to about 30 cm.

* * * * *